US008426492B2

(12) United States Patent
Lu

(10) Patent No.: US 8,426,492 B2
(45) Date of Patent: Apr. 23, 2013

(54) OXIDIZED CATIONIC POLYSACCHARIDE-BASED POLYMER TISSUE ADHESIVE FOR MEDICAL USE

(75) Inventor: Helen S. M. Lu, Wallingford, PA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 351 days.

(21) Appl. No.: 12/742,457

(22) PCT Filed: Nov. 14, 2008

(86) PCT No.: PCT/US2008/083522
§ 371 (c)(1),
(2), (4) Date: May 12, 2010

(87) PCT Pub. No.: WO2009/064963
PCT Pub. Date: May 22, 2009

(65) Prior Publication Data
US 2010/0272804 A1    Oct. 28, 2010

Related U.S. Application Data

(60) Provisional application No. 61/003,059, filed on Nov. 14, 2007.

(51) Int. Cl.
*A61K 6/097* (2006.01)
*A61K 9/00* (2006.01)
*A61K 31/715* (2006.01)

(52) U.S. Cl.
USPC ............ 523/118; 424/488; 424/486; 514/54; 525/509

(58) Field of Classification Search ................... 523/118; 424/488, 486; 514/54; 525/509
See application file for complete search history.

(56) References Cited

U.S. PATENT DOCUMENTS

| | | | |
|---|---|---|---|
| 4,584,188 A | 4/1986 | Graham | |
| 4,703,116 A | 10/1987 | Solarek et al. | |
| 4,731,162 A | 3/1988 | Solarek et al. | |
| 4,741,804 A | 5/1988 | Solarek et al. | |
| 4,749,800 A | 6/1988 | Jobe et al. | |
| 4,766,245 A | 8/1988 | Larkin et al. | |
| 5,092,883 A | 3/1992 | Eppley et al. | |
| 5,116,824 A | 5/1992 | Miyata et al. | |
| 5,162,430 A | 11/1992 | Rhee et al. | |
| 5,196,441 A | 3/1993 | Kunisch et al. | |
| 5,275,838 A | 1/1994 | Merrill | |
| 5,292,802 A | 3/1994 | Rhee et al. | |
| 5,308,889 A | 5/1994 | Rhee et al. | |
| 5,324,775 A | 6/1994 | Rhee et al. | |
| 5,328,995 A | 7/1994 | Schaulin et al. | |
| 5,451,398 A | 9/1995 | Vigh | |
| 5,502,042 A | 3/1996 | Gruskin et al. | |
| 5,505,952 A | 4/1996 | Jiang et al. | |
| 5,514,379 A | 5/1996 | Weissleder et al. | |
| 5,567,685 A | 10/1996 | Linden et al. | |
| 5,643,575 A | 7/1997 | Martinez et al. | |
| 5,733,563 A | 3/1998 | Fortier | |
| 5,776,706 A * | 7/1998 | Siiman et al. ................ 435/7.21 |
| 5,830,986 A | 11/1998 | Merrill et al. | |
| 5,840,698 A | 11/1998 | Campbell et al. | |
| 5,843,865 A | 12/1998 | Del Corral et al. | |
| 5,874,500 A | 2/1999 | Rhee et al. | |
| 6,051,648 A | 4/2000 | Rhee et al. | |
| 6,121,375 A | 9/2000 | Eknoian | |
| 6,150,472 A | 11/2000 | Engbers | |
| 6,165,488 A | 12/2000 | Tardy et al. | |
| 6,166,130 A | 12/2000 | Rhee et al. | |
| 6,323,278 B2 | 11/2001 | Rhee et al. | |
| 6,391,939 B2 | 5/2002 | Tayot et al. | |
| 6,410,519 B1 | 6/2002 | Gruskin et al. | |
| 6,458,147 B1 | 10/2002 | Cruise et al. | |
| 6,458,889 B1 | 10/2002 | Trollsas et al. | |
| 6,465,694 B1 | 10/2002 | Baudys et al. | |
| 6,514,534 B1 | 2/2003 | Sawhney | |
| 6,534,591 B2 | 3/2003 | Rhee et al. | |
| 6,602,952 B1 | 8/2003 | Bentley et al. | |
| 6,620,125 B1 | 9/2003 | Redl | |
| 6,696,089 B2 | 2/2004 | Kabanov et al. | |
| 6,703,047 B2 | 3/2004 | Sawhney et al. | |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

Thome, J. et al., "Ultrathin Antibacterial Polyammonium Coatings on Polymer Surfaces"; Surface and Coatings Technology, 174-175, 2003, pp. 584-587.

Harris, J. Milton, "Laboratory Synthesis of Polyethylene Glycol Derivatives", JMS—Rev., Macromol. Chem. Phys., C25 (3), 1985, pp. 325-373.

Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.

Chen, Nicole, et al., "Mechanisms of Aldehyde-Containing Paper Wet-Strength Resins", Industrial & Engineering Chemistry Research, vol. 41, No. 22, 2002, pp. 5366-5371.

Callant, Dominique, et al., "A New Approach to Dextran Derivatives with Pendent Aldehyde Groups", Reactive Polymers, vol. 8, 1988, pp. 129-136.

(Continued)

*Primary Examiner* — Michael Pepitone
(74) *Attorney, Agent, or Firm* — McCarter and English

(57) ABSTRACT

A tissue adhesive formed by reacting an oxidized cationic polysaccharide containing aldehyde groups and amine groups with a multi-arm amine is described. The oxidized cationic polysaccharide-based polymer tissue adhesive may be useful for medical applications including wound closure, supplementing or replacing sutures or staples in internal surgical procedures such as intestinal anastomosis and vascular anastomosis, ophthalmic procedures, drug delivery, anti-adhesive applications and as a bulking agent to treat urinary incontinence. Additionally, due to the presence of the positively charged amine groups on the oxidized polysaccharide, the polymer tissue adhesive disclosed herein may promote wound healing and blood coagulation, and may possess antimicrobial properties.

25 Claims, No Drawings

U.S. PATENT DOCUMENTS

| | | | |
|---|---|---|---|
| 6,756,518 | B2 | 6/2004 | Gruskin et al. |
| 6,800,278 | B1 | 10/2004 | Perrault et al. |
| 6,833,408 | B2 | 12/2004 | Sehl et al. |
| 6,858,736 | B2 | 2/2005 | Nho et al. |
| 7,217,845 | B2 | 5/2007 | Rosen et al. |
| 7,834,065 | B2 | 11/2010 | Nakajima et al. |
| 2002/0151520 | A1 | 10/2002 | Gruskin |
| 2003/0022216 | A1 | 1/2003 | Mao |
| 2003/0027788 | A1 | 2/2003 | Singh et al. |
| 2003/0064502 | A1 | 4/2003 | Illman et al. |
| 2003/0087111 | A1 | 5/2003 | Hubbell et al. |
| 2003/0108511 | A1 | 6/2003 | Sawhney |
| 2003/0119985 | A1 | 6/2003 | Sehl et al. |
| 2004/0086479 | A1 | 5/2004 | Grinstaff et al. |
| 2004/0096507 | A1 | 5/2004 | Kwang et al. |
| 2004/0225097 | A1 | 11/2004 | Nho et al. |
| 2004/0235708 | A1 | 11/2004 | Rhee et al. |
| 2005/0002893 | A1 | 1/2005 | Goldmann |
| 2005/0020805 | A1 | 1/2005 | Sunkara et al. |
| 2005/0288684 | A1 | 12/2005 | Aronson et al. |
| 2006/0078536 | A1 | 4/2006 | Kodokian et al. |
| 2006/0115531 | A1 | 6/2006 | Chenault |
| 2006/0292030 | A1 | 12/2006 | Odermatt et al. |
| 2007/0031467 | A1 | 2/2007 | Abrahams et al. |
| 2007/0048251 | A1 | 3/2007 | Arthur |
| 2007/0249870 | A1 | 10/2007 | Chenault |
| 2008/0004421 | A1 | 1/2008 | Chenault et al. |
| 2008/0220047 | A1 | 9/2008 | Sawhney et al. |
| 2008/0319101 | A1 | 12/2008 | Nakajima et al. |
| 2009/0035249 | A1 | 2/2009 | Bhatia et al. |
| 2009/0054535 | A1* | 2/2009 | Figuly et al. ............ 514/772.7 |
| 2010/0086678 | A1 | 4/2010 | Arthur et al. |
| 2010/0112063 | A1* | 5/2010 | Figuly et al. ................ 424/486 |
| 2010/0272804 | A1 | 10/2010 | Lu |

FOREIGN PATENT DOCUMENTS

| | | |
|---|---|---|
| JP | 1988-11167 | 1/1988 |
| WO | WO 87/00836 | 2/1987 |
| WO | WO 90/10441 | 9/1990 |
| WO | WO 91/15368 | 10/1991 |
| WO | WO 97/30103 | 8/1997 |
| WO | WO 99/01143 | 1/1999 |
| WO | WO 00/69925 | 11/2000 |
| WO | WO 01/49268 | 7/2001 |
| WO | WO 01/72280 | 10/2001 |
| WO | WO 01/87986 | 11/2001 |
| WO | WO 02/102864 | 12/2002 |
| WO | WO 03/020818 | 3/2003 |
| WO | WO 03/097759 | 11/2003 |
| WO | WO 2006/031358 | 3/2006 |
| WO | WO 2006/042161 | 4/2006 |
| WO | WO 2006/080523 | 8/2006 |
| WO | WO 2006/086510 | 8/2006 |
| WO | WO 2008/005207 | 1/2008 |
| WO | WO 2008/066787 | 6/2008 |
| WO | WO 2009/064977 | 5/2009 |
| WO | WO 2010/059279 | 5/2010 |
| WO | WO 2010/059280 | 5/2010 |
| WO | WO 2010/111570 | 9/2010 |
| WO | WO 2010/118284 | 10/2010 |

OTHER PUBLICATIONS

Hollander, Andreas, et al., "Polymer Surface Chemistry for Biologically Active Materials", Applied Surface Science, vol. 235, 2004, pp. 145-150.

Stone, H. Harlan, et al., "Antibiotic Prophylaxis in Gastric, Biliary and Colonic Surgery", Ann. Surg; Oct. 1976, pp. 443-450.

Fishman, Alexander, et al., "Synthesis and Investigation of Novel Branched PEG-Based Soluble Polymer Supports", The Journal of Organic Chemistry, vol. 68, 2003, pp. 9843-9846.

Newkome, George R., "Improved Synthesis of an Ethereal Tetraamine Core for Dendrimer Construction", The Journal of Organic Chemistry, vol. 67, 2002, pp. 3957-3960.

Halabi, A., et al., "Synthesis and Characterization of a Novel Dendritic Acrylic Monomer", The Journal of Organic Chemistry, vol. 65, 2000, pp. 9210-9213.

Harris, J. Milton, et al., "Synthesis and Characterization of Poly(ethylene Glycol) Derivatives", Journal of Polymer Science: Polymer Chemistry Edition, vol. 22, 1984, pp. 341-352.

Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.

Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.

Azzam, Tony, et al., "Cationic Polysaccharides for Gene Delivery", Macromolecules, vol. 35, No. 27, 2002, pp. 9947-9953.

Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.

Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.

Zalipsky, Samuel, et al., "Preparation and Applications of Polyethylene Glycol—Polystyrene Graft Resin Supports for Solid-Phase Peptide Synthesis", Reactive Polymers, vol. 22, 1994, pp. 243-258.

Lara, V.S., et al., "Dentin-Induced In Vivo Inflammatory Response and In Vitro Activation of Murine Macrophages", Journal of Dental Research, vol. 82, No. 6, 2003, pp. 460-465.

Atassi, M.Z., "Immunochemistry of Proteins", vol. 1, Plenum Press, New York, 1977, pp. 59-60.

Sweeney, Thomas, et al., "Intestinal Anastomoses Detected with a Photopolymerized Hydrogel", Surgery, vol. 131, No. 2, Feb. 2002, pp. 185-189.

Kim, Jae Chan, et al., "Evaluation of Tissue Adhesives in Closure of Scleral Tunnel Incisions", Journal of Cataract & Refractive Surgery, vol. 21, May 1995, pp. 320-325.

Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.

Buckmann, Andreas F., et al., "Functionalization of Poly(ethylene glycol) and Monomethoxy-Poly(ethylene glycol)", Makromolecular Chemistry, vol. 182, 1981, pp. 1379-1384.

Bruce, J., et al., "Systematic Review of the Definition and Measurement of Anastomotic Leak after Gastrointestinal Surgery", British Journal of Surgery, vol. 88, 2001, pp. 1157-1168.

Mo, Xiumei, et al,, "Soft Tissue Adhesive Composed of Modified Gelatin and Polysaccharides", Journal of Biomaterials Science Polymer Edition, vol. 11, No. 4, 2000, pp. 341-351.

Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.

Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.

Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.

Pfannemuller, B., et al., "Chemical Modification of the Surface of the Starch Granules", Starch/Starke, vol. 95, No. 9, 1983, pp. 298-303.

Specification of U.S. Appl. No. 13/102,262.

* cited by examiner

OXIDIZED CATIONIC POLYSACCHARIDE-BASED POLYMER TISSUE ADHESIVE FOR MEDICAL USE

CROSS-REFERENCE TO RELATED APPLICATION

This application is a 35 U.S.C. §371 national state filing of International Application No. PCT/US2008/083522, filed Nov. 14, 2008, which claims priority under 35 U.S.C. §119 from U.S. Provisional Application Ser. No. 61/003,059, filed Nov. 14, 2007. The entire contents of each of the foregoing applications are incorporated herein by reference.

FIELD OF THE INVENTION

The invention relates to the field of medical adhesives. More specifically, the invention relates to a polymer tissue adhesive formed by reacting an oxidized cationic polysaccharide containing aldehyde groups and amine groups with a multi-arm amine.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the Fibrin-based adhesives do not covalently bind to the underlying tissue.

Several types of hydrogel tissue adhesives have been developed, which have improved adhesive and cohesive properties and are nontoxic. These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell or dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. However, a tissue adhesive having these properties in addition to also having a cationic charge to promote wound healing and blood coagulation, while providing antimicrobial properties would be highly desirable.

Oxidized crosslinked polysaccharides having a chemically induced charge have been reported to be useful for treating wounds (Gruskin et al., U.S. Pat. No. 5,502,042) and for reducing scar formation (Gruskin et al. U.S. Pat. Nos. 6,410,519 and 6,756,518). Additionally, a polysaccharide-based hydrogel formed by reacting oxidized dextran and chitosan for use as a tissue adhesive is described by Goldmann (U.S. Patent Application Publication No. 2005/0002893) and Odermatt et al. (U.S. Patent Application Publication No. 2006/0292030).

Therefore, the problem to be solved is to provide a tissue adhesive material with improved adhesion and cohesion properties, that crosslinks readily at body temperature, maintains dimensional stability initially, does not degrade rapidly, is nontoxic to cells and non-inflammatory to tissue, and has a cationic charge for use in surgical procedures as well as other medical applications. The stated problem is addressed herein by the discovery that hydrogels formed by reaction of an oxidized cationic polysaccharide containing aldehyde groups and amine groups with a multi-arm amine possess these desired properties.

SUMMARY OF THE INVENTION

An embodiment provides a kit comprising:
a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; and
b) at least one water-dispersible, multi-arm amine wherein at least three of the arms are terminated by a primary amine group, wherein the multi-arm amine has a number-average molecular weight of about 450 to about 200,000 Daltons.

Another embodiment provides the kit, wherein the oxidized polysaccharide is a first aqueous solution or dispersion and the multi-arm amine is a second aqueous solution or dispersion.

In yet another embodiment, the kit, wherein the oxidized polysaccharide and the multi-arm amine are finely divided powders.

In yet another embodiment, the kit, wherein the oxidized polysaccharide containing aldehyde groups and amine groups is derived from a polysaccharide selected from the group consisting of dextran, carboxymethyldextran, starch, agar, cellulose, hydroxyethylcellulose, carboxymethylcellulose, pullulan, inulun, levan, agarose, and hyaluronic acid.

Another embodiment provides the kit, wherein the oxidized polysaccharide containing aldehyde groups and amine groups is oxidized diethylaminoethyl dextran or oxidized aminated dextran.

Another embodiment provides the kit, wherein the multi-arm amine is selected from the group consisting of water dispersible multi-arm polyether amines, amino-terminated dendritic polyamidoamines, and branched end amines.

In yet another embodiment the kit, wherein the water dispersible multi-arm polyether amines are selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

Another embodiment provides the kit, wherein the oxidized polysaccharide containing aldehyde groups and amine groups is oxidized diethylaminoethyl dextran or oxidized aminated dextran and the multi-arm amine is a multi-arm polyethylene glycol amine.

An embodiment provides a dried hydrogel product formed by a process comprising the steps of:
a) reacting in a solvent (i) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; with (ii) at least one water-dispersible, multi-arm amine wherein at least three of the arms are terminated by a primary amine group, wherein the multi-arm amine has a number-average molecular weight of about 450 to about 200,000 Daltons to form a hydrogel; and
b) treating the hydrogel to remove at least a portion of said solvent to form the dried hydrogel.

Another embodiment provides the dried hydrogel, wherein said dried hydrogel is a film.

Another embodiment provides the dried hydrogel, wherein the process further comprises the step of comminuting the dried hydrogel to form finely divided particles.

In yet another embodiment, the dried hydrogel, wherein the oxidized polysaccharide containing aldehyde groups and amine groups is derived from a polysaccharide selected from the group consisting of dextran, carboxymethyldextran, starch, agar, cellulose, hydroxyethylcellulose, carboxymethylcellulose, pullulan, inulun, levan, agarose, and hyaluronic acid.

In yet another embodiment, the dried hydrogel, wherein the oxidized polysaccharide containing aldehyde groups and amine groups is oxidized diethylaminoethyl dextran or oxidized aminated dextran.

Another embodiment provides the dried hydrogel, wherein the multi-arm amine is selected from the group consisting of water dispersible multi-arm polyether amines, amino-terminated dendritic polyamidoamines, and branched end amines.

In yet another embodiment, the kit, wherein the water dispersible multi-arm polyether amines are selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

In yet another embodiment the dried hydrogel, wherein the oxidized polysaccharide is oxidized diethylaminoethyl dextran or oxidized aminated dextran and the multi-arm amine is a multi-arm polyethylene glycol amine.

An embodiment provides a method for coating an anatomical site on tissue of a living organism comprising:
applying to the site
a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; followed by
b) at least one water-dispersible, multi-arm amine wherein at least three of the arms are terminated by a primary amine group, wherein the multi-arm amine has a number-average molecular weight of about 450 to about 200,000 Daltons; or alternatively, applying (b) followed by (a) and mixing (a) and (b) on the site, or alternatively, premixing (a) and (b) and applying the resulting mixture to the site.

Another embodiment provides the method, wherein the oxidized polysaccharide is a first aqueous solution or dispersion and the multi-arm amine a second aqueous solution or dispersion.

In yet another embodiment, the method, wherein the oxidized polysaccharide and the multi-arm amine are finely divided powders.

In yet another embodiment, the method, wherein the oxidized polysaccharide is oxidized diethylaminoethyl dextran or oxidized aminated dextran and the multi-arm amine is a multi-arm polyethylene glycol amine.

An embodiment provides a method for bonding at least two anatomical sites together comprising:
applying to at least one of the at least two anatomical sites:
a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50; followed by
b) at least one water-dispersible, multi-arm amine wherein at least three of the arms are terminated by a primary amine group, wherein the multi-arm amine has a number-average molecular weight of about 450 to about 200,000 Daltons; or alternatively, applying (b) followed by (a) and mixing (a) and (b) on the at least one site, or alternatively premixing (a) and (b) and applying the resulting mixture to the at least one site and contacting the at least two anatomical sites together.

Another embodiment provides the method, wherein the oxidized polysaccharide is a first aqueous solution or dispersion and the multi-arm amine is a second aqueous solution or dispersion.

Another embodiment provides the method, wherein the oxidized polysaccharide and the multi-arm amine are finely divided powders.

Another embodiment provides the method, wherein the oxidized polysaccharide is oxidized diethylaminoethyl dextran or oxidized aminated dextran and the multi-arm amine is a multi-arm polyethylene glycol amine.

In yet another embodiment, the method for applying a coating to an anatomical site on tissue of a living organism comprising:
applying to the site the dried hydrogel.

In yet another embodiment, the method, wherein said dried hydrogel is a film.

In yet another embodiment, the method, wherein said dried hydrogel is finely divided particles.

An embodiment of the invention provides a combination for use in coating an anatomical site, the combination comprising:
a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; followed by b) at least one water-dispersible, multi-arm amine wherein at least three of the arms are terminated by a primary amine group, wherein the multi-arm amine has a number-average molecular weight of about 450 to about 200,000 Daltons; or alternatively, (b) followed by (a).

Another embodiment provides the combination, wherein the oxidized polysaccharide is a first aqueous solution or dispersion and the multi-arm amine is a second aqueous solution or dispersion.

Another embodiment provides the combination, wherein the oxidized polysaccharide and the multi-arm amine are finely divided powders.

In yet another embodiment, the combination, wherein the oxidized polysaccharide is oxidized diethylaminoethyl dextran or oxidized aminated dextran and the multi-arm amine is a multi-arm polyethylene glycol amine.

An embodiment provides a combination for use in bonding at least two anatomical sites together, wherein the combination is applied to at least one of the at least two anatomical sites, the combination comprising:

a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50; followed by b) at least one water-dispersible, multi-arm amine wherein at least three of the arms are terminated by a primary amine group, wherein the multi-arm amine has a number-average molecular weight of about 450 to about 200,000 Daltons; or alternatively, (b) followed by (a).

Another embodiment provides the combination, wherein the oxidized polysaccharide is a first aqueous solution or dispersion and the multi-arm amine is a second aqueous solution or dispersion.

In yet another embodiment, the combination, wherein the oxidized polysaccharide and the multi-arm amine are finely divided powders.

In yet another embodiment, the combination, wherein the oxidized polysaccharide is oxidized diethylaminoethyl dextran or oxidized aminated dextran and the multi-arm amine is a multi-arm polyethylene glycol amine.

An embodiment provides a product for use in coating an anatomical site comprising the dried hydrogel.

Another embodiment provides the product, wherein said dried hydrogel is a film.

In yet another embodiment, the product, wherein said dried hydrogel is finely divided particles.

DETAILED DESCRIPTION OF THE INVENTION

Disclosed herein is a polymer tissue adhesive formed by reacting at least one oxidized polysaccharide containing aldehyde groups and amine groups, wherein the amine groups are not primary amine groups, with a multi-arm amine. The polymer tissue adhesive may be useful for medical applications including, but not limited to, wound closure, surgical procedures, such as intestinal anastomosis, vascular anastomosis, tissue repair, and ophthalmic procedures; drug delivery, anti-adhesive applications, and as a bulking agent to treat urinary incontinence. Due to the presence of the positively charged amine groups on the oxidized polysaccharide, the polymer tissue adhesive disclosed herein may promote wound healing and blood coagulation, and may possess antimicrobial properties.

The following definitions are used herein and should be referred to for interpretation of the claims and the specification.

The term "oxidized polysaccharide" refers to a polysaccharide that has been reacted with an oxidizing agent to introduce aldehyde groups into the molecule.

The term "equivalent weight per aldehyde group" refers to the average molecular weight of the compound divided by the number of aldehyde groups in the molecule.

The term "amine substitution level" as used herein, refers to the percent of saccharide rings of a polysaccharide that are substituted with a nitrogen containing group which is not a primary amine group. The amine substitution level is determined using proton nuclear magnetic resonance (NMR) spectroscopy, as described herein.

The term "water-dispersible, multi-arm amine" refers to a polymer having three or more polymer chains ("arms"), which may be linear or branched, emanating from a central structure, which may be a single atom, a core molecule, or a polymer backbone, wherein at least three of the branches ("arms") are terminated by a primary amine group. The water-dispersible, multi-arm amine is water soluble or is able to be dispersed in water to form a colloidal suspension capable of reacting with a second reactant in aqueous solution or dispersion.

The term "water-dispersible, multi-arm polyether amine" refers to a branched polyether, wherein at least three of the branches ("arms") are terminated by a primary amine group, which is water soluble or able to be dispersed in water to form a colloidal suspension capable of reacting with a second reactant in aqueous solution or dispersion.

The term "polyether" refers to a polymer having the repeat unit [—O—R]—, wherein R is a hydrocarbylene group having 2 to 5 carbon atoms.

The term "branched polyether" refers to a polyether having one or more branch points ("arms"), including star, dendritic, comb, highly branched, and hyperbranched polyethers.

The term "dendritic polyether" refers to a highly branched polyether having a branching structure that repeats regularly with each successive generation of monomer, radiating from a core molecule.

The term "comb polyether" refers to a multi-arm polyether in which linear side chains emanate from trifunctional branch points on a linear polymer backbone.

The term "star polyether" refers to a multi-arm polyether in which linear side chains emanate from a single atom or a core molecule having a point of symmetry.

The term "highly branched polyether" refers to a multi-arm polyether having many branch points, such that the distance between branch points is small relative to the total length of the arms.

The term "hyperbranched polyether" refers to a multi-arm polyether that is more branched than highly branched with order approaching that of an imperfect dendritic polyether.

The term "branched end amine" refers to a linear or multi-arm polymer having two or three primary amine groups at each of the ends of the polymer chain or at the end of the polymer arms.

The term "hydrogel" refers to a water-swellable polymeric matrix, consisting of a three-dimensional network of macromolecules held together by covalent or non-covalent crosslinks that can absorb a substantial amount of water to form an elastic gel.

The term "dried hydrogel" refers to a hydrogel that has been treated to remove at least a portion of the solvent contained therein. Preferably, substantially all of the solvent is removed from the hydrogel.

The term "% by weight", also referred to herein as "wt %", as used herein refers to the weight percent relative to the total weight of the solution or dispersion, unless otherwise specified.

The term "anatomical site" refers to any external or internal part of the body of humans or animals.

The term "tissue" refers to any tissue, both living and dead, in humans or animals.

The term "medical application" refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "wt %" means percent by weight, "mol %" means mole percent, "Vol" means volume, "v/v" means volume per volume, "Da" means Daltons, "kDa" means kiloDaltons, the designation "10K" means that a polymer molecule possesses a number-average molecular weight of 10 kiloDaltons, "M" means molarity, "MWCO" means molecular weight cut-off, "kPa" means kilopascals, "$^1$H NMR" means proton nuclear magnetic resonance spectroscopy, "ppm" means parts per million, "$M_w$" means weight-average molecular weight, "$M_n$" means number-average molecular weight, "PBS" means phosphate-buffered saline, "PEG' means polyethylene glycol".

A reference to "Aldrich" or a reference to "Sigma" means the said chemical or ingredient was obtained from Sigma-Aldrich, St. Louis, Mo.

Oxidized Polysaccharides Containing Aldehyde Groups and Amine Groups

The polysaccharides useful in the invention are oxidized to contain aldehyde groups and also contain amine groups, which are not primary amine groups. Specifically, the amine groups may be secondary, tertiary, or quaternary amines. It is preferred that the amine groups are not reactive with the aldehyde groups on the oxidized polysaccharide so that there is no substantial crosslinking of the polysaccharide with itself.

The oxidized polysaccharides containing aldehyde groups and amine groups may be derived from various polysaccharides by chemical modification using methods known in the art, as described below. Suitable starting polysaccharides include, but are not limited to, dextran, carboxymethyldextran, starch, agar, cellulose, hydroxyethylcellulose, carboxymethylcellulose, pullulan, inulun, levan, agarose, and hyaluronic acid. These polysaccharides are available commercially from sources such as Sigma-Aldrich (Milwaukee, Wis.) and Pharmacosmos A/S (Holbaek, Denmark). Typically, commercial preparations of polysaccharides are a heterogeneous mixture having a distribution of different molecular weights and are characterized by various molecular weight averages, for example, the weight-average molecular weight, or the number-average molecular weight, as is known in the art. Suitable polysaccharides have a weight-average molecular weight of about 1,000 to about 1,000,000 Daltons, preferably from about 3,000 to about 500,000 Daltons.

The polysaccharide may be modified to contain amine groups by various chemical reactions. A modified polysaccharide containing amine groups is also referred to herein as an aminated polysaccharide. For example, the polysaccharide may be reacted with various amine containing electrophiles, e.g., glycidyl trimethyl ammonium chloride or diethylaminoethyl chloride, to yield the corresponding amine-containing polysaccharide. In one embodiment, the polysaccharide is reacted with diethylaminoethyl chloride as described by Gruskin et al. (U.S. Pat. No. 5,502,042), which introduces diethylaminoethyl (DEAE) groups. Alternatively, polysaccharides containing amine groups may be obtained commercially, for example DEAE dextran, DEAE cellulose, and DEAE agarose are available from commercial sources such as Sigma-Aldrich. Furthermore, the polysaccharide may first be oxidized to introduce aldehyde groups, as described below, which are subsequently reacted with amines under reductive conditions to yield the corresponding amine-containing polysaccharide.

The amine substitution level of the polysaccharide is determined using proton NMR by determining the ratio of the integral of the peak corresponding to the pendant amine groups to the sum of the integrals of the peaks corresponding to the anomeric protons of the glucose ring and comparing it to the expected ratio for a fully derivatized product, as shown in the Examples herein.

The amine-containing polysaccharide may be oxidized to contain aldehyde groups using methods known in the art. Oxidized polysaccharides may be prepared by oxidation of amine-containing polysaccharides using any suitable oxidizing agent, including but not limited to, periodates, hypochlorites, ozone, peroxides, hydroperoxides, persulfates, and percarbonates. In one embodiment, the amine-containing polysaccharide is oxidized by reaction with sodium periodate, for example as described by Mo et al. (*J. Biomater. Sci. Polymer Edn.* 11:341-351, 2000). The amine-containing polysaccharide may be reacted with different amounts of periodate to give polysaccharides with different degrees of oxidation and therefore, different amounts of aldehyde groups, as described in detail in the General Methods Section of the Examples herein. The aldehyde content of the oxidized amine-containing polysaccharide may be determined using methods known in the art. For example, the dialdehyde content of the oxidized amine-containing polysaccharide may be determined using the method described by Hofreiter et al. (*Anal Chem.* 27:1930-1931, 1955), as described in detail in the General Methods Section of the Examples herein. In that method, the amount of alkali consumed per mole of dialdehyde in the oxidized amine-containing polysaccharide, under specific reaction conditions, is determined by a pH titration.

Suitable oxidized polysaccharides containing aldehyde groups and amine groups have a weight-average molecular weight of about 1,000 to about 1,000,000 Daltons, preferably from about 3,000 to about 500,000 Daltons; an equivalent weight per aldehyde group of about 90 to about 1500 Daltons; and an amine substitution level of about 5% to about 50%.

In one embodiment, the oxidized polysaccharide containing aldehyde groups and amine groups is oxidized DEAE dextran having a weight-average molecular weight of about 120,000 Daltons, an equivalent weight per aldehyde group of about 246 Daltons, and an amine substitution level of about 33% (one in 3 glucose units).

In another embodiment, the oxidized polysaccharide containing aldehyde groups and amine groups is oxidized DEAE dextran having a weight-average molecular weight of about 6400 Daltons, an equivalent weight per aldehyde group of about 213 Daltons, and an amine substitution level of about 33% (one in 3 glucose units).

In another embodiment, the oxidized polysaccharide containing aldehyde groups and amine groups is oxidized DEAE dextran having a weight-average molecular weight of about 61,000 Daltons, an equivalent weight per aldehyde group of about 411 Daltons, and an amine substitution level of about 33% (one in 3 glucose units).

In another embodiment, the oxidized polysaccharide containing aldehyde groups and amine groups is an oxidized aminated dextran having a weight-average molecular weight of about 60,000 to about 90,000 Daltons, an equivalent weight per aldehyde group of about 452 Daltons, and an amine substitution level of about 19%.

In another embodiment, the oxidized polysaccharide containing aldehyde groups and amine groups is an oxidized aminated dextran having a weight-average molecular weight of about 60,000 to about 90,000 Daltons, an equivalent weight per aldehyde group of about 923 Daltons, and an amine substitution level of about 38%.

In another embodiment, the oxidized polysaccharide containing aldehyde groups and amine groups is an oxidized aminated dextran having a weight-average molecular weight of about 60,000 to about 90,000 Daltons, an equivalent weight per aldehyde group of about 164 Daltons, and an amine substitution level of about 12%.

In another embodiment, the oxidized polysaccharide containing aldehyde groups and amine groups is an oxidized aminated dextran having a weight-average molecular weight of about 60,000 to about 90,000 Daltons, an equivalent weight per aldehyde group of about 156 Daltons, and an amine substitution level of about 18%.

Water-Dispersible, Multi-Arm Amines

Suitable water dispersible, multi-arm amines include, but are not limited to, water dispersible multi-arm polyether amines, amino-terminated dendritic polyamidoamines, and branched end amines. Typically, the multi-arm amines have a number-average molecular weight of about 450 to about 200,000 Daltons, more specifically, from about 2,000 to about 40,000 Daltons.

In one embodiment, the water dispersible, multi-arm amine is a multi-arm polyether amine, which is a water-dispersible polyether having the repeat unit [—O—R]—, wherein R is a hydrocarbylene group having 2 to 5 carbon atoms. The term "hydrocarbylene group" refers to a divalent group formed by removing two hydrogen atoms, one from each of two different carbon atoms, from a hydrocarbon. Suitable multi-arm polyether amines include, but are not limited to, dendritic, comb, star, highly branched, and hyper-branched polyethers wherein at least three of the arms are terminated by a primary amine group. Examples of water-dispersible, multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines sold under the trade name Jeffamine® triamines, by Huntsman LLC. (Houston, Tex.). Examples of star polyethylene oxide amines, include, but are not limited to, various multi-arm polyethylene glycol amines, available from Nektar Transforming Therapeutics (Huntsville, Ala.), and star polyethylene glycols having 3, 4, 6, or 8 arms terminated with primary amines (referred to herein as 3, 4, 6 or 8-arm star PEG amines, respectively). The 8-arm star PEG amine is available from Nektar Transforming Therapeutics. Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible multi-arm polyether amine is an eight-arm polyethylene glycol having eight arms terminated by a primary amine group and having a number-average molecular weight of about 10,000 Daltons.

The multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Additionally, multi-arm polyether amines may be prepared from multi-arm polyols using the method described by Chenault (copending and commonly owned U.S. Patent Application Publication No. 2007/0249870). In that method, the multi-arm polyether is reacted with thionyl chloride to convert the hydroxyl groups to chlorine groups, which are then converted to amines by reaction with aqueous or anhydrous ammonia. Other methods that may be used for preparing multi-arm polyether amines are described by Merrill et al. in U.S. Pat. No. 5,830,986, and by Chang et al. in WO 97/30103.

The multi-arm amine may also be an amino-terminated dendritic polyamidoamine, sold under the trade name Starburst® Dendrimers (available from Sigma-Aldrich, St Louis, Mo.).

The multi-arm amine may also be a branched end amine, as described by Arthur (copending and commonly owned Patent Application No. PCT/US07/24393, WO 2008/066787). The branched end amines can be linear or branched polymers having two or three amine groups at each of the ends of the polymer chain or at the end of the polymer arms. The multiplicity of functional groups increases the statistical probability of reaction at a given chain end and allows more efficient incorporation of the linear or branched molecules into a polymer network. The starting materials used to prepare the branched end amines may be linear polymers such as polyethylene oxide, poly(trimethyleneoxide), block or random copolymers of polyethylene oxide and polypropylene oxide or triblock copolymers of polyethylene oxide and polypropylene oxide, having terminal hydroxyl groups, or branched polymers such as multi-arm polyether polyols including, but not limited to, comb and star polyether polyols. The branched end amines can be prepared by attaching multiple amine groups to the ends of the polymer using methods well known in the art. For example, a branched end amine having two amine functional groups on each end of the polymer chain or at the end of the polymer arms can prepared by reacting the starting material, as listed above, with thionyl chloride in a suitable solvent such as toluene to give the chloride derivative, which is subsequently reacted with tris(2-aminoethyl) amine to give the branched end reactant having two amino groups at each end of the polymer chain or arm.

It should be recognized that the multi-arm amines are generally a somewhat heterogeneous mixture having a distribution of arm lengths and in some cases, a distribution of species with different numbers of arms. When a multi-arm amine has a distribution of species having different numbers of arms, it can be referred to based on the average number of arms in the distribution. For example, in one embodiment the multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm amines, should be construed as referring to a heterogeneous mixture having a distribution of arm lengths and in some cases, a distribution of species with different numbers of arms, in which case the number of arms recited refers to the average number of arms in the mixture.

In one embodiment, the oxidized polysaccharide containing aldehyde groups and amine groups is oxidized DEAE dextran and the multi-arm amine is a multi-arm polyethylene glycol amine.

In another embodiment, the oxidized polysaccharide containing aldehyde groups and amine groups is an oxidized aminated dextran and the multi-arm amine is a multi-arm polyethylene glycol amine.

Methods of Using the Polymer Tissue Adhesive

The polymer tissue adhesive disclosed herein may be used in various forms. In one embodiment, the oxidized polysaccharide containing aldehyde groups and amine groups and the multi-arm amine are used in the form of aqueous solutions or dispersions. Dispersion, as used herein, refers to a colloidal suspension capable of reacting with a second reactant in an aqueous medium. To prepare an aqueous solution or dispersion comprising at least one oxidized polysaccharide containing aldehyde groups and amine groups (referred to herein as the "first aqueous solution or dispersion"), at least one oxidized polysaccharide containing aldehyde groups and amine groups is added to water to give a concentration of about 5% to about 70% by weight, specifically about 5% to about 50% by weight; more specifically about 10% to about 50% by weight; and more specifically about 10% to about 30% by weight, relative to the total weight of the solution or dispersion. Mixtures of different oxidized polysaccharides containing aldehyde groups and amine groups, having different average molecular weights and/or different equivalent weights per aldehyde group, and/or different amine substitution levels may also be used. If a mixture of different oxidized polysaccharides containing aldehyde groups and amine groups is used, the total concentration of the polysaccharides is about 5% to about 70% by weight, specifically about 5% to about 50% by weight, more specifically about 10% to about 50% by weight, and more specifically about 10% to about 30% by weight, relative to the total weight of the solution or dispersion.

To prepare an aqueous solution or dispersion comprising at least one multi-arm amine (referred to herein as the "second aqueous solution or dispersion"), at least one multi-arm amine is added to water to give a concentration of about 5% to about 50% by weight, specifically from about 15% to about 50% by weight, relative to the total weight of the solution or dispersion. Mixtures of different multi-arm amines may also be used. If a mixture of different multi-arm amines is used, the total concentration of the multi-arm amines is about 5% to about 50% by weight, specifically about 15% to about 50% by weight, relative to the total weight of the solution or dispersion. The optimal concentrations of the two aqueous solutions or dispersions to be used depend on the application, and can be readily determined by one skilled in the art using routine experimentation.

For use on living tissue, it is preferred that the first aqueous solution or dispersion and the second aqueous solution or dispersion be sterilized to prevent infection. Any suitable sterilization method known in the art that does not adversely affect the ability of the components to react to form an effective hydrogel may be used, including, but not limited to, electron beam irradiation, gamma irradiation, ethylene oxide sterilization, or ultra-filtration through a 0.2 μm pore membrane.

The first aqueous solution or dispersion and/or the second aqueous solution or dispersion may further comprise various additives depending on the intended application. Preferably, the additive is compatible with the other components of the solution. Specifically, the additive does not contain groups that would interfere with effective gelation of the hydrogel. The amount of the additive used depends on the particular application and may be readily determined by one skilled in the art using routine experimentation. For example, the first aqueous solution or dispersion and/or the second aqueous solution or dispersion may comprise at least one additive selected from pH modifiers, viscosity modifiers, antimicrobials, colorants, surfactants, pharmaceutical drugs and therapeutic agents.

The solution(s) or dispersion(s) may optionally include at least one pH modifier to adjust the pH of the solution(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution(s) or dispersion(s) may optionally include at least one thickener. The thickener may be selected from among known viscosity modifiers, including, but not limited to, polysaccharides and derivatives thereof, such as starch or hydroxyethyl cellulose.

The aqueous solution(s) or dispersion(s) may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may also optionally include at least one colorant to enhance the visibility of the solution(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The aqueous solution(s) or dispersion(s) may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution(s) or dispersion(s) may optionally include at least one pharmaceutical drug or therapeutic agent. Suitable drugs and therapeutic agents are well known in the art (for example see the United States Pharmacopeia (USP), Physician's Desk Reference (Thomson Publishing), *The Merck Manual of Diagnosis and Therapy* 18th ed., Mark H. Beers and Robert Berkow (eds.), Merck Publishing Group, 2006; or, in the case of animals, *The Merck Veterinary Manual,* 9th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

Additionally, the second aqueous solution or dispersion comprising the multi-arm amine may optionally comprise at least one other multi-functional amine having one or more primary amine groups to provide other beneficial properties, such as hydrophobicity or modified crosslink density. The multi-functional amine is capable of inducing gelation when mixed with an oxidized polysaccharide in an aqueous solution or dispersion. Suitable multi-functional amines include, but are not limited to, linear and branched diamines, such as diaminoalkanes, polyaminoalkanes, and spermine; branched polyamines, such as polyethylenimine; cyclic diamines, such as N,N'-bis(3-aminopropyl)piperazine, 5-amino-1,3,3-trimethylcyclohexanemethylamine, 1,3-bis(aminomethyl)cyclohexane, 1,4-diaminocyclohexane, and p-xylylenediamine; aminoalkyltrialkoxysilanes, such as 3-aminopropyltrimethoxysilane and 3-aminopropyltriethoxysilane; aminoalkyldialkoxyalkylsilanes, such as 3-aminopropyldiethoxymethylsilane, dihydrazides, such as adipic dihydrazide; linear polymeric diamines, such as linear polyethylenimine, $\alpha,\omega$-amino-terminated polyethers, $\alpha,\omega$-bis(3-aminopropyl)polybutanediol, $\beta,\omega$-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm amine in the aqueous solution or dispersion.

In another embodiment, the multi-functional amine is provided in a separate solution at a concentration of about 5% by weight to about 100% by weight relative to the total weight of the solution. If the multi-functional amine is not used neat (i.e., 100% by weight), it is used in the form of an aqueous solution or dispersion. For use on living tissue, it is preferred that the solution comprising the multi-functional amine be sterilized. Any of the methods described above for sterilizing the first and second aqueous solutions or dispersions may be used. The aqueous solution or dispersion comprising the multi-functional amine may further comprise various additives. Any of the additives described above may be used.

The first aqueous solution or dispersion and the second aqueous solution or dispersion may be applied to an anatomical site on tissue of a living organism in any number of ways. Once both solutions or dispersions are applied to a site, they crosslink to form a hydrogel, a process referred to herein as curing, typically in about 2 seconds to about 2 minutes.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the two aqueous solutions or dispersions are contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). Additionally, the double barrel syringe may contain a motionless mixer, such as that available from ConProtec, Inc. (Salem, N.H.) or Mixpac Systems AG (Rotkreuz, Switzerland), at the tip to effect mixing of the two aqueous solutions or dispersions prior to application. Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055). Suitable delivery devices for use in ophthalmic applications, where small volumes of the two aqueous solutions or dispersions or the mixture thereof are required, are also known in the art (see for example Miller et al., U.S. Pat. No. 4,874,368, and copending and commonly owned U.S. Patent Application No. 61/002,071).

In another embodiment, the first aqueous solution or dispersion and the second aqueous solution or dispersion are applied to the site simultaneously where they mix to form a hydrogel. The two aqueous solutions or dispersions may be applied to the site in various ways, for example, using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the polymer tissue adhesive of the invention is used to bond at least two anatomical sites together. In this embodiment, the first aqueous solution or dispersion is applied to at least one anatomical site, and the second aqueous solution or dispersion is applied to at least one of either the same site or one other site. The two or more sites are contacted and held together manually or using some other means, such as a surgical clamp, for a time sufficient for the mixture to cure, typically from about 2 seconds to about 2 minutes. Alternatively, a mixture of the two aqueous solutions or dispersions either premixed manually or using a double-barrel syringe applicator, is applied to at least one of the anatomical sites to be bonded. The two or more sites are contacted and held together manually or using some other means, such as a surgical clamp, for a time sufficient for the mixture to cure.

In another embodiment, the oxidized polysaccharide containing aldehyde groups and amine groups and the multi-arm amine are used in the form of finely divided powders. The powders may be prepared using any suitable method. For example, the aqueous solutions described above may be dried using heat, vacuum, a combination of heat and vacuum, or by lyophilization, to form powders. Optionally, the powders may be comminuted into finer particles using methods known in the art including, but not limited to, grinding, milling, or crushing with a mortar and pestle. The finely divided powders may be sterilized using the methods described above. The finely divided powders may be applied to an anatomical site on tissue of a living organism in a variety of ways. For example, the powders may be individually applied to the site in any order by sprinkling or spraying. Additionally, the two powders may be premixed and the resulting mixture applied to the site using the methods described above. The powders may be hydrated on the site by the addition of a suitable buffer (e.g., phosphate-buffered saline) or by the physiological fluids present at the site. The finely divided powders may also be used to bond two anatomical sites together as described above for the aqueous solutions or dispersions.

In another embodiment, the polymer tissue adhesive disclosed herein is used in the form of a dried hydrogel. In this embodiment, a hydrogel is prepared by mixing a first solution or dispersion comprising at least one oxidized polysaccharide containing aldehyde groups and amine groups with a second solution or dispersion comprising at least one multi-arm amine to form the hydrogel. The solutions or dispersions may be prepared in any suitable solvent, including but not limited to, water, ethanol, isopropanol, tetrahydrofuran, hexanes, polyethylene glycol, and mixtures thereof. If a mixture of solvents is used, it is preferable to use solvents that are miscible with each other. In one embodiment, the solvent is water. The solutions or dispersions may further comprise various additives depending on the intended application. Any of the additives described above may be used. The hydrogel is then treated to remove at least a portion of the solvent contained therein to form the dried hydrogel. Preferably, substantially all of the solvent is removed from the hydrogel. The solvent may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above. The dried hydrogel may be applied to an anatomical site in a number of ways, as described below. The dried hydrogel may be hydrated on the site by the addition of a suitable buffer (e.g., phosphate-buffered saline) or by the physiological fluids present at the site.

In one embodiment, the dried hydrogel is used in the form of a film. The dried hydrogel film may be formed by casting a mixture of the first and second solutions or dispersions, as described above, on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel is used in the form of finely divided particles. The dried hydrogel particles may be formed by comminuting the dried hydrogel using methods known in the art, including, but not limited to, grinding, milling, or crushing with a mortar and pestle. The dried hydrogel may be applied to an anatomical site in a variety of ways, such as sprinkling or spraying, and may also be used to bond two anatomical sites together.

Kits

In one embodiment, the invention provides a kit comprising at least one oxidized polysaccharide containing aldehyde groups and amine groups and at least one multi-arm amine, as described above.

In one embodiment, the kit comprises at least one oxidized polysaccharide containing aldehyde groups and amine groups and at least one multi-arm amine in the form of aqueous solutions or dispersions, as described above. Each of the aqueous solutions or dispersions may be contained in any suitable vessel, such as a vial or a syringe barrel.

In another embodiment, the kit comprises at least one oxidized polysaccharide containing aldehyde groups and amine groups and at least one multi-arm amine in the form of finely divided powders, as described above. The powders may be contained in separate containers or they may be premixed and contained in a single container. The kit may also comprise a buffer solution for hydrating the powders.

In another embodiment, the kit comprises a dried hydrogel formed by reacting a first solution or dispersion comprising at least one oxidized polysaccharide containing aldehyde groups and amine groups in a suitable solvent with a second solution or dispersion comprising at least one multi-arm amine in a suitable solvent, as described above. The dried hydrogel may be in the form of a film, finely divided particles, or other dried forms. The kit may further comprise a buffer for hydrating the dried hydrogel. The dried hydrogel particles may be contained in any suitable container.

Medical Applications

The polymer tissue adhesive disclosed herein has many potential medical applications, including, but not limited to, wound closure, supplementing or replacing sutures or staples in internal surgical procedures such as intestinal anastomosis and vascular anastomosis, ophthalmic procedures, drug delivery, anti-adhesive applications and as a bulking agent to treat urinary incontinence, as described by Kodokian et al. (copending and commonly owned U.S. Patent Application Publication No. 2006/0078536).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

All water used in these Examples was distilled-deionized water unless otherwise stated.

General Methods

Preparation of Oxidized Dextrans Containing Aldehyde Groups and Amine Groups: Preparation of Oxidized DEAE Dextran Having a Dialdehyde Content of 41% and an Amine Substitution Level of 33%

In a round-bottom flask, 20 g of DEAE-dextran hydrochloride (diethylaminoethyl-dextran hydrochloride, having an amine substitution of about 1 in 3 glucose units, i.e., about 33% substitution; Sigma, product D9885) was dissolved in 180 mL of water. Sodium periodate solution (19 g in 160 mL of water) was added to the flask over a period of 30 min using an addition funnel. The reaction mixture was stirred at room temperature overnight, after which time, it turned dark brown. Ethylene glycol (a 10-fold molar excess relative to the amount of sodium periodate in the reaction mixture) was added to the mixture, which was then stirred for another hour. The reaction mixture was dialyzed 10 times with water using MWCO 3500 dialysis tubing. The first five dialysis steps were done using 100 mL of sample in 1 L of water. The next five dialysis steps, which appeared to be more effective in removing residual iodides, as indicated by the clearing of the color in the dialysis tube, were done using 50 mL of sample in 1 L of water. The dialysates were combined and lyophilized to yield 3.3 g of white solid.

$^1$H NMR ($D_2O$): 1.30 ppm (multiplet, integration 1), 3.1-3.9 ppm (broad multiplet, integration 4.5), 5.1-5.94 ppm (broad multiplet, integration 1.42). Size exclusion chromatography (SEC) analysis of the product gave $M_w=1.2\times10^5$ and $M_w/M_n=13.88$.

The dialdehyde content in the resulting oxidized DEAE dextran was determined using the following procedure. The oxidized DEAE dextran (0.1 to 0.3 g) was added to 10 mL of 0.25 M NaOH in a 250 mL Erlenmeyer flask. The mixture was gently swirled and then placed in a temperature-controlled sonicator bath at 40° C. for 5 min until all the material dissolved, giving a dark yellow solution. The sample was removed from the bath and the flask was cooled under cold tap water for 5 min. Then 15.00 mL of 0.25 M HCl was added to the solution, followed by the addition of 50 mL of water and 1 mL of 0.2% phenolphthalein solution. This solution was titrated with 0.25 M NaOH to an endpoint determined by a color change from yellow to purple/violet. The same titration was carried out on a sample of the starting DEAE dextran to afford a background aldehyde content. The dialdehyde content, also referred to herein as the oxidation conversion or the degree of oxidation, in the oxidized DEAE dextran sample was calculated using the following formula:

$$\text{Dialdehyde Content} = \frac{(Vb-Va)_s}{W_s/M_w} - \frac{(Vb-Va)_p}{W_p/M_w} \times 100\%$$

Vb=total meq of base
Va=total meq of acid
W=dry sample weight (mg)
$M_w$=weight-average molecular weight of polysaccharide repeat unit (=189 for DEAE dextran)
s=oxidized sample
p=original sample A dialdehyde content of 41% was obtained, which corresponds to an equivalent weight per aldehyde group of about 246 Daltons.

Preparation of Oxidized DEAE Dextran Having a Dialdehyde Content of 47% and an Amine Substitution Level of 33%

In a round-bottom flask, 20 g of DEAE-dextran hydrochloride (having an amine substitution of about 1 in 3 glucose units, i.e., about 33% substitution; Sigma, product D9885) was dissolved in 200 mL of water. Sodium periodate solution (40 g in 400 mL of water) was added to the flask over a period of 30 min using an addition funnel. The reaction mixture was stirred at room temperature overnight, after which time, it turned dark brown. Ethylene glycol (a 10-fold molar excess relative to the amount of sodium periodate in the reaction mixture) was added to the mixture, which was then stirred for another hour. The reaction mixture was dialyzed 5 times with water using MWCO 3500 dialysis tubing. The dialysates were combined, and 100 g of sodium chloride was added. This solution was desalted using a tangential flow filtration (TFF) ultrafiltration unit (Pellicon 2/Pellicon cassette system from Millipore Corp., Billerica, Mass.) using a MWCO 1000 membrane by filtration with 2 L of 5 M NaCl, followed by an 8× volume of water. The filtrate was lyophilized to yield 3.1 g of white solid.

The dialdehyde content of the product was determined to be 47% by titration, as described above, which corresponds to an equivalent weight per aldehyde group of about 213 Daltons.

$^1$H NMR ($D_2O$): 1.30 ppm (multiplet, integration 1), 3.1-3.9 ppm (broad multiplet, integration 3.9), 5.1-5.9 ppm (broad multiplet, integration 1.2). SEC analysis of the product gave $M_w=6.4\times10^3$ and $M_w/M_n=1.8$.

Preparation of Oxidized DEAE Dextran Having a Dialdehyde Content of 25% and an Amine Substitution Level of 33%

In a 500 mL round-bottom flask, 20 g of DEAE dextran hydrochloride (having an amine substitution of about 1 in 3 glucose units, i.e., about 33% substitution; Sigma, product D9885) was dissolved in 180 mL of water. To the flask, sodium periodate solution (9.4 g in 80 mL of water) was added. The mixture was stirred at room temperature for 5 h, then immediately filtered using a TFF filtration system (Pelicon cartridges, MWCO 1000). A 7× volume of filtrate was collected, which was very brown in color. The reaction solution changed from an amber brown to a clear, colorless solution during filtration; however the solution developed a slight yellow tinge when allowed to sit at room temperature overnight. The sample was lyophilized to dryness to yield 10 g of pale yellow solid.

The dialdehyde content of the product was determined to be 25% by titration, as described above, which corresponds to an equivalent weight per aldehyde group of about 411 Daltons.

The product was further purified by ultrafiltration as follows. A solution of the product was prepared by dissolving 4.6 g in 5 M NaCl (400 mL). The solution was filtered with a TFF filtration system (Pelicon cartridges, MWCO 1000). A 5× volume (2 L) of 5 M NaCl, was first used to filter the sample. The sodium chloride solution used was found to have undissolved salt remaining in the container. Based on the remaining weight of NaCl, the molarity of the solution was determined to be approximately 3.5 M. The sample was then filtered with an 8× volume (3.2 L) of water and subsequently lyophilized to give 2.8 g of yellow solid.

The iodine content was determined to be 92 ppm by elemental analysis. SEC analysis of the product gave $M_w$=6.1×10$^4$ and $M_w/M_n$=7.52.

Preparation of Oxidized DEAE Dextran Having a Dialdehyde Content of 67% and an Amine Substitution Level of 33%

In a 500 mL round-bottom flask, 20 g of DEAE dextran hydrochloride (having an amine substitution of about 1 in 3 glucose units, i.e., about 33% substitution; Sigma, product D9885) was dissolved in 200 mL of water. To the flask, sodium periodate solution (40 g in 400 mL of water) was added over 30 min using an addition funnel. The mixture was stirred at room temperature overnight in the dark. Ethylene glycol (1.87 mol) was added and the mixture was stirred for another hour. The reaction mixture was ultrafiltered using a TFF filtration system (Pelicon cartridges, MWCO 1000) with collection of a 2.0 L eluant volume. Sodium chloride (100 g) was added to the ultrafiltered reaction mixture, and the solution was further ultrafiltered with collection of a 10× volume of eluant volume. The reaction mixture was lyophilized to yield 17.4 g of white solid. The dialdehyde content of the product was determined to be 67% by titration, as described above, which corresponds to an equivalent weight per aldehyde group of about 126 Daltons.

Preparation of Oxidized Dextran Having a Dialdehyde Content of 20% and an Amine Substitution Level of 19%

An oxidized dextran having a dialdehyde content of 20% and an amine substitution level of 19% was prepared using a two step procedure. First an aminated dextran was prepared by reacting dextran with glycidyl triethylammonium chloride. Then, the aminated dextran was oxidized by reaction with sodium periodate to give the aminated dextran aldehyde.

In a round bottom flask, 10 g of dextran (weight-average molecular weight of 60 kDa to 90 kDa, Sigma) was dissolved in 37.5 mL of sodium hydroxide solution (20 wt % in water), and the resulting solution was then chilled to 0° C. To this chilled solution was added 14.0 mL of glycidyl trimethylammonium chloride (CAS No. 3033-77-0, Aldrich, catalog no. 50053) in portions. This mixture was heated at 40° C. for 60 h, and then cooled to room temperature. The yellow homogeneous mixture was neutralized with 50% HCl over ice, dialyzed against water (4 times), and freeze dried to yield 6.7 g of white solid.

$^1$H NMR (D$_2$O): 3.24 ppm (singlet, integration 1), 3.5-4.42 ppm (broad multiplet, integration 3.85), 4.42 ppm (broad singlet, 0.10), 4.97 ppm (broad, integration 0.49), 5.15 ppm (broad, integration 0.07), 5.32 ppm (broad, integration 0.02).

The level of amine substitution was determined by $^1$H NMR to be 19%, by calculating the ratio of the integral at 3.24 ppm (N(CH$_3$)$_3$) to the sum of the integrals at 4.97, 5.15, and 5.32 ppm (anomeric protons) and comparing it to the expected ratio for a fully derivatized product (expected ratio is 9:1).

The aminated dextran product (3.0 g) was dissolved in 30 mL of water in a 100 mL round-bottom flask. To this solution was added a sodium periodate suspension (2.7 g in 20 mL of water). The resulting mixture was stirred at room temperature for 5 h, and then 7.0 mL of ethylene glycol was added. The mixture was stirred at room temperature for 30 min, then dialyzed using water with MWCO 3500 dialysis tubing with 4 water exchanges. The product was lyophilized to yield 1.46 g of white powder. The dialdehyde content was determined by titration as described above for the DEAE dextran, using a weight-average molecular weight of polysaccharide repeat unit of 180 for the modified dextran. The dialdehyde content was found to be 20%, which corresponds to an equivalent weight per aldehyde group of about 452 Daltons.

Preparation of Oxidized Dextran Having a Dialdehyde Content of 9.5% and an Amine Substitution Level of 38%

An oxidized dextran having a dialdehyde content of 9.5% and an amine substitution level of 38% was prepared using a two step procedure. First an aminated dextran was prepared by reacting dextran with glycidyl triethylammonium chloride. Then, the aminated dextran was oxidized by reaction with sodium periodate to give the aminated dextran aldehyde.

In a round bottom flask, 10 g of dextran (weight-average molecular weight of 60 kDa to 90 kDa, Sigma) was dissolved in 27.5 mL of sodium hydroxide solution (20 wt % in water). To this solution was added 28.0 mL of glycidyl trimethylammonium chloride (CAS No. 3033-77-0, Aldrich, catalog no. 50053) in portions. The resulting mixture was heated at 40° C. for 60 h, and then cooled to room temperature. The yellow homogeneous mixture was neutralized with 50% HCl over ice, dialyzed against water (4 times), and freeze dried to yield 5.3 g of white solid.

$^1$H NMR (D$_2$O): 3.24 ppm (singlet, integration 1.0), 3.5-4.42 ppm (broad multiplet, integration 2.1), 4.25 ppm (br, 0.08), 4.42 ppm (broad singlet, 0.10), 4.97 ppm (broad, integration 0.26), 5.15 ppm (broad, integration 0.02), 5.32 (broad, integration 0.01).

The level of amine substitution was determined by $^1$H NMR to be 38%, by calculating the ratio of the integral at 3.24 ppm (N(CH$_3$)$_3$) to the sum of the integrals at 4.97, 5.15, and 5.32 ppm (anomeric protons) and comparing it to the expected ratio for a fully derivatized product (expected ratio is 9:1).

The aminated dextran product (3.0 g) was dissolved in 30 mL of water in a 100 mL round-bottom flask. To this solution was added a sodium periodate suspension (2.7 g in 20 mL of water). The resulting mixture was stirred at room temperature for 5 h, then dialyzed using water with MWCO 3500 dialysis tubing with 4 water exchanges. The product was lyophilized to yield 0.49 g of white powder. The dialdehyde content was determined by titration, as described above, to be 9.5%, which corresponds to an equivalent weight per aldehyde group of about 923 Daltons.

Preparation of Oxidized Dextran Having a Dialdehyde Content of 49% and an Amine Substitution Level of 12%

An oxidized dextran having a dialdehyde content of 49% and an amine substitution level of 12% was prepared using a two step procedure. First an aminated dextran was prepared by reacting dextran with glycidyl triethylammonium chloride. Then, the aminated dextran was oxidized by reaction with sodium periodate to give the aminated dextran aldehyde.

In a round bottom flask, 10 g of dextran (weight-average molecular weight of 60 kDa to 90 kDa, Sigma) was dissolved in 25 mL of sodium hydroxide solution (20 wt % in water). To this solution was added 14.0 mL of glycidyl trimethylammonium chloride (CAS No. 3033-77-0, Aldrich, catalog no. 50053) in portions. The resulting mixture was heated at 40° C. for 24 h, and then cooled to room temperature. Another 14.0 mL of glycidyl trimethylammonium chloride was added and the mixture was heated at 40° C. for another 60 h. The yellow homogeneous mixture was neutralized with 50% HCl over ice, dialyzed against water (4 times), and freeze dried to yield 7.0 g of white solid.

$^1$H NMR (D$_2$O): 3.24 ppm (singlet, integration 1.98), 3.5-3.99 ppm (multiplet, integration 11.13), 4.43 ppm (broad singlet, 0.63), 4.98 ppm (broad, integration 1.57), 5.16 ppm (broad, integration 0.18), 5.32 (broad, integration 0.16).

The level of amine substitution was determined by $^1$H NMR to be 12% by calculating the ratio of the integral at 3.24 ppm (N(CH$_3$)$_3$) to the sum of the integrals at 4.98, 5.16, and 5.32 ppm (anomeric protons) and comparing it to the expected ratio for a fully derivatized product (expected ratio is 9:1).

The aminated dextran product (3.0 g) was dissolved in 30 mL of water in a 100 mL round-bottom flask. To this solution was added a sodium periodate suspension (5.4 g in 20 mL of water). The resulting mixture was stirred at room temperature for 5 h, then dialyzed using water with MWCO 3500 dialysis tubing with 4 water exchanges. The product was lyophilized to yield 0.59 g of white powder. The dialdehyde content was determined by titration, as described above, to be 49%, which corresponds to an equivalent weight per aldehyde group of about 164 Daltons.

Preparation of Oxidized Dextran Having a Dialdehyde Content of 51% and an Amine Substitution Level of 18%

An oxidized dextran having a dialdehyde content of 51% and an amine substitution level of 18% was prepared using a two step procedure. First an aminated dextran was prepared by reacting dextran with epichlorohydrin and N,N'-dimethylethylamine. Then, the aminated dextran was oxidized by reaction with sodium periodate to give the aminated dextran aldehyde.

In a round bottom flask was added 5 g of dextran (weight-average molecular weight of 60 kDa to 90 kDa, Sigma), 3.66 mL of epichlorohydrin (Aldrich), 3.4 g of N,N'-dimethylethylamine (Aldrich), and 10 mL of water. This mixture was stirred at room temperature overnight, and then heated at 50° C. for 8 h. The sample was neutralized with 50% HCl and dialyzed against water (4 times) using MWCO 3500 dialysis tubing. The dialysates were combined and freeze dried to yield 6.4 g solid.

$^1$H NMR (D$_2$O): 1.40 ppm (singlet, integration 1.0), 3.19 ppm (singlet, integration 1.86), 3.5-4.20 ppm (broad multiplet, integration 9.1), 4.45 ppm (br, 0.51), 4.97 ppm (broad, integration 0.78), 5.17 ppm (broad, integration 0.14).

The level of amine substitution was determined by $^1$H NMR to be 18%, by calculating the ratio of the integral at 1.40 ppm (N(CH$_3$)$_2$CH$_2$CH$_3$) to the sum of the integrals at 4.97, and 5.17 ppm (anomeric protons) and comparing it to the expected ratio for a fully derivatized product (expected ratio 6:1).

The aminated dextran product (3.0 g) was dissolved in 30 mL of water in a 100 mL round-bottom flask. To this solution was added a sodium periodate suspension (2.85 g in 28 mL of water). The resulting mixture was stirred at room temperature for 5 h, then dialyzed using water with MWCO 3500 dialysis tubing with 4 water exchanges. The product was lyophilized to yield 0.45 g of white powder. The dialdehyde content was determined by titration, as described above, to be 51%, which corresponds to an equivalent weight per aldehyde group of about 156 Daltons.

Preparation of Multi-Arm Peg Amine

Preparation of 8-Arm Polyethylene Glycol 10K Octaamine (P8-10-1)

An 8-arm PEG 10K octaamine, referred to herein as "P8-10-1," was synthesized using the two-step procedure described by Chenault in copending and commonly owned U.S. Patent Application Publication No. 2007/0249870. A typical synthesis is described here. In the first step, the 8-arm PEG 10K was converted to an 8-Arm PEG 10K chloride by reaction with thionyl chloride, i.e.,

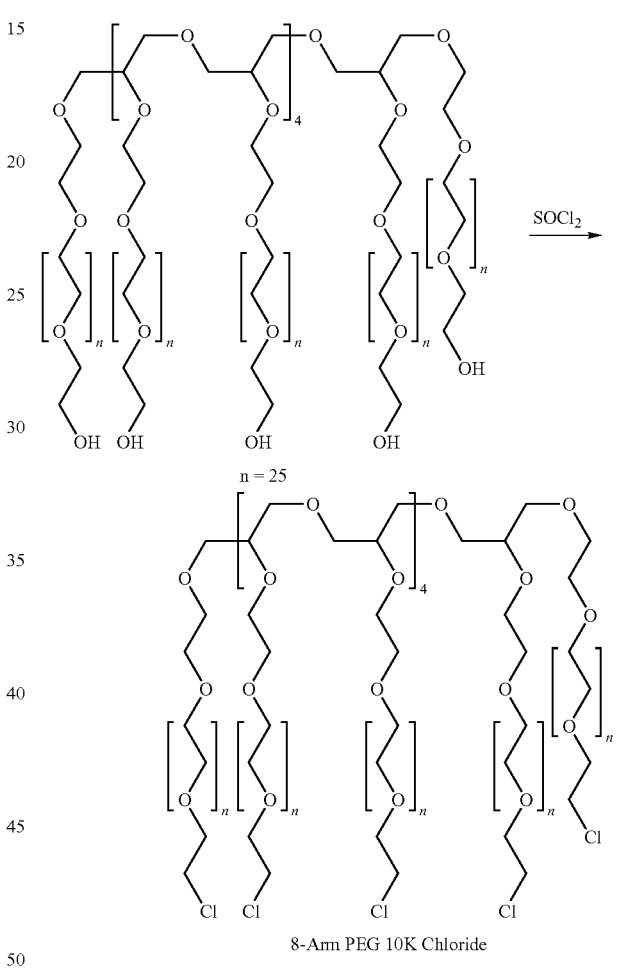

8-Arm PEG 10K Chloride

The 8-arm PEG 10K (NOF Sunbright HGEO-10000; 1000 g in a 3-L round-bottom flask) was dried by dissolving it in 1.5 L of toluene and distilling 500 mL of toluene-water azeotrope plus toluene under reduced pressure (2 kPa) with a pot temperature of 60° C., adding another 500 mL of toluene to the pot, and distilling 500 mL of toluene-water azeotrope plus toluene under reduced pressure (2 kPa) with a pot temperature of 60° C.

The solution of 8-arm PEG was allowed to cool to room temperature. Then, thionyl chloride (233 mL, 3.19 mol) was added to the flask, which was equipped with a reflux condenser, and the mixture was heated at 85° C. with stirring under a blanket of nitrogen for 4 h. Excess thionyl chloride and most of the toluene were removed by vacuum distillation at 2 kPa (bath temp 40-60° C.). Two successive 500-mL portions of toluene were added and evaporated under reduced pressure (2 kPa, bath temperature 80-85° C.) to complete the removal of thionyl chloride. The final crude product was dissolved in 1000 g of de-ionized water.

In the second step, the 8-Arm PEG 10K chloride was converted to the 8-Arm PEG 10K amine by reaction with aqueous ammonia, i.e.,

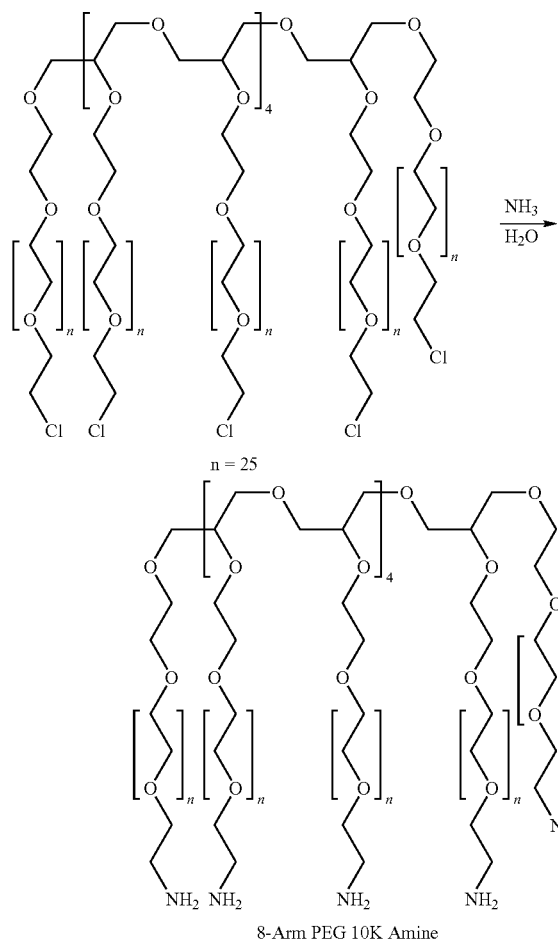

8-Arm PEG 10K Amine

The aqueous solution of 8-arm PEG-Cl prepared above, was dissolved in 16 L of concentrated aqueous ammonia (28 wt %) and heated in a sealed stainless steel pressure vessel at 60° C. for 48 h. The solution was sparged for 24 h with dry nitrogen and then placed under reduced pressure for 3 h to drive off ammonia. The solution was then passed through a column of strongly basic anion exchange resin (5 kg; Purolite® A-860, The Purolite Co., Bala-Cynwyd, Pa.) in the hydroxide form. The eluant was collected, and two 7-L portions of de-ionized water were passed through the column and collected. The aqueous fractions were combined, concentrated under reduced pressure (2 to 0.3 kPa, bath temperature 60° C.) to give the 8-Arm PEG 10K octaamine. The final product was characterized by proton NMR and size exclusion chromatography (SEC), as described by Chenault, supra.

Examples 1-3

Preparation of Hydrogels from Reaction of Oxidized Deae-Dextrans Containing Aldehyde Groups and Amine Groups with a Multi-Arm PEG Amine The following Examples demonstrate the preparation of hydrogels from reaction of a multi-arm PEG amine with oxidized DEAE-dextran containing aldehyde groups and amine groups. The gel time to form the hydrogels was measured.

Into a small vial, 100 µL of an aqueous DEAE dextran aldehyde stock solution (20 wt %), as disclosed in Table 1, was added. The DEAE dextran aldehydes having various degrees of dialdehyde content were prepared as described in General Methods. The vial was tilted and 100 µL of a 50 wt % aqueous multi-arm PEG amine solution (P8-10-1), prepared as described in General Methods, was added with care taken not to mix the two solutions. A timer was started and the two solutions were stirred together with the wooden end of a cotton swab. The initial gel time was defined as the observation of increased viscosity, such that a string formed when the wooden stirring rod was pulled from the gel. The final gel time was defined as the second when stirring pulled the gel from the sides of the vial so that the gel could be removed as the wooden stirring rod was pulled from the vial.

The initial and final gel times are given in Table 1. The final gel times ranged from 6 to 22 sec, depending on the concentration and oxidation conversion of the DEAE dextran aldehyde used.

TABLE 1

Gel Times for Forming Hydrogels Prepared from DEAE-Dextran Aldehyde and P8-10-1 PEG Amine

| Example | DEAE-Dextran Aldehyde Solution | Initial Gel Time (sec) | Final Gel Time (sec) |
| --- | --- | --- | --- |
| 1 | 41% dialdehyde content | 3 | 6 |
| 2 | 47% dialdehyde content | 1 | 7 |
| 3 | 25% dialdehyde content | 4 | 22 |

Examples 4 and 5

In Vitro Biocompatibility Testing—Cytotoxicity

The following Examples demonstrate the safety of hydrogels resulting from the reaction of a multi-arm PEG amine with a DEAE dextran aldehyde in an in vitro test.

The testing was done using NIH3T3 mouse fibroblast cell cultures according to ISO10993-5:1999. The NIH3T3 mouse fibroblast cells were obtained from the American Type Culture Collection (ATCC; Manassas, Va.) and were grown in Dulbecco's modified essential medium (DMEM), supplemented with 10% fetal calf serum.

NIH3T3 mouse fibroblast cell cultures were challenged with hydrogels made by combining equal volumes of an aqueous solution of a DEAE-dextran aldehyde and an aqueous solution of a multi-arm PEG amine, as shown in Table 2. Each hydrogel was placed in a well in a polystyrene culture plate such that about ¼ of the well bottoms were covered. The wells were then sterilized under UV light and seeded with 50,000-100,000 NIH3T3 cells.

The cells grew normally confluent and coated the well bottom, growing up to the edges of the hydrogels; however, they did not overgrow the hydrogels. These results, summarized in Table 2, demonstrate a lack of cytotoxicity of the hydrogels, as well as the lack of adhesion of cell cultures to the hydrogels.

TABLE 2

Cytotoxicity Results

| Example | DEAE Dextran Aldehyde Solution | Multi-Arm PEG Amine Solution | Cytotoxicity |
|---|---|---|---|
| 4 | 25% dialdehyde content, 10 wt % solution | P8-10-1 30 wt % | nontoxic |
| 5 | 25% dialdehyde content, 10 wt % solution | P8-10-1 50 wt % | nontoxic |

Examples 6-8

In-Vitro Burst Testing of a Sealed Scalpel Incision

The following Examples demonstrate the burst strength of a seal made with various hydrogels of an incision made in swine uterine horn.

A syringe pump system was used to measure the burst strength of a seal of an incision made in a section of swine uterine uterine horn. The syringe pump (Model No. 22, Harvard Apparatus, Holliston, Mass.) was modified to be equipped with two 30 mL syringes, which were connected together through a "Y" junction. Water was pumped through a single piece of Tygon® R-36 tubing (0.6 cm diameter) and through a pressure gauge (Model PDG 5000L, Omega Engineering, Stamford, Conn.).

An approximately 12.5 cm section of swine uterine horn obtained from a local abattoir, was fitted on one end with a metal plug with a feed line fitting for water feed from the syringe pump and on the other end with a metal plug with a threaded hole which could be sealed with a machine screw. The plugs were held in place with nylon ties around the outside of the uterine horn. An incision was made through the uterine horn wall into the interior by puncturing with a Bard Parker™ surgical blade handle 5 (obtained from BD Surgical Products, Franklin Lakes, N.J.), fitted with a #15 surgical blade. The incision on the outside of the uterine horn was wider than the scalpel blade (typically 4-5 mm) while the hole through the inside wall was about 3 mm (about equal to the blade). This size incision mimics the distance between the interrupted sutures if an intestine were to be cut and later sutured. The uterine horn was filled with water containing a purple dye via the syringe pump until water began to leak from the open hole in the end plug and also from the scalpel puncture in the uterine horn wall. The pump was then turned off and the end plug was sealed with the machine screw. The scalpel incision site was blotted dry using a paper towel.

The DEAE dextran aldehyde and multi-arm PEG amine solutions were prepared in water. The two solutions were applied to the incision using a double barrel syringe (Mixpac Systems AG (Rotkreuz, Switzerland) fitted with a 16 step static mixer (Mixpac Systems AG). After the application, the adhesive was allowed to cure at room temperature for no longer than 2 min.

Burst pressure testing, also referred to herein as leak pressure testing, was done by pressurizing the sealed uterine horn with water from the syringe pump at a flow rate of 11 mL/min until the bioadhesive seal began to leak, at which point the pressure was recorded. Adhesive failure was attributed when the water leaked under the seal between the hydrogel and the tissue surface. Cohesive failure was attributed when the water penetrated and leaked through the hydrogel itself. Burst pressure testing was also done on the unsealed uterine horn and the leak pressure was less than 10 mm of mercury (Hg) (less than 1.3 kPa).

The results of the burst testing are summarized in Table 3. The results demonstrate that the hydrogels formed by reaction of various DEAE-dextran aldehyde and multi-arm PEG amine solutions were able to seal the incision in swine uterine horn.

TABLE 3

Burst Pressure Testing Results

| Example | DEAE-Dextran Aldehyde Solution | Multi-Arm PEG Amine Solution (P8-10-1) | Ave Burst Pressure, mm Hg | Standard Deviation Burst Pressure, mm Hg |
|---|---|---|---|---|
| 6 | 25% dialdehyde content, 20 wt % solution | 50 wt % | 113 (15.1 kPa) | 22.9 (3.0 kPa) |
| 7 | 41% dialdehyde content, 20 wt % solution | 50 wt % | 168 (22.3 kPa) | 96.8 (12.9 kPa) |
| 8 | 47% dialdehyde content, 20 wt % solution | 50 wt % | 209 (27.9 kPa) | 37.9 (5.0 kPa) |

Examples 9-11

In Vitro Degradation of Hydrogels

The following Examples demonstrate that the hydrogels formed by reaction of a DEAE-dextran aldehyde with a multi-arm PEG amine degrade in vitro.

The hydrogel samples were prepared by mixing equal volumes of an aqueous solution of a DEAE-dextran aldehyde and an aqueous solution of a multi-arm PEG amine, as shown in Table 4. After the hydrogels cured, the samples were weighed and placed inside jars containing PBS at pH 7.4. The jars were placed inside a temperature-controlled shaker set at 80 rpm and 37° C. The samples were removed from the jars at various times, blotted to remove excess solution, and weighed. Then, the samples were returned to the jars.

The results are summarized in Table 4. The percent swell reported in the table is the weight of the hydrogel at the specified time divided by the initial weight of the hydrogel, multiplied by 100. The results indicate that the hydrogels swell and degrade in vitro.

TABLE 4

Results of In Vitro Degradation of Hydrogels

| | | Multi-Arm PEG- | | | | |
| | DEAE-Dextran | Amine | | % Swell | | |
| | Aldehyde | Solution | | | | |
| Example | Solution | (P8-10-1) | 5 h | 48 h | 72 h | 168 h |
|---|---|---|---|---|---|---|
| 9 | 25% dialdehyde content, 20 wt % solution | 50 wt % | 0* | 0 | 0 | 0 |
| 10 | 41% dialdehyde content, 20 wt % solution | 50 wt % | 503 | 576 | 518 | 366 |
| 11 | 47% dialdehyde content, 20 wt % solution | 50 wt % | 305 | 336 | 336 | 333 |

TABLE 4-continued

Results of In Vitro Degradation of Hydrogels

| Example | DEAE-Dextran Aldehyde Solution | Multi-Arm PEG-Amine Solution (P8-10-1) | % Swell | | | |
|---|---|---|---|---|---|---|
| | | | 5 h | 48 h | 72 h | 168 h |
| 12 | 67% dialdehyde content, 12 wt % solution | 30 wt % | 320 | 225 | not measured | 151 |

*The hydrogel degraded in less than 5 hours.

Examples 13-16

Preparation of Hydrogels from Reaction of Oxidized Dextrans Containing Aldehyde Groups and Amine Groups with a Multi-Arm PEG Amine The following Examples demonstrate the preparation of hydrogels from reaction of an oxidized dextran containing aldehyde groups and amine groups with a multi-arm PEG amine. The gel time to form the hydrogels was measured.

Into a small vial was added 100 μL of an aqueous stock solution containing 20 wt % of an oxidized dextran having aldehyde groups and amine groups (aminated dextran aldehyde), as given in Table 5. The oxidized dextrans having various levels of dialdehyde content and amine substitution were prepared as described in General Methods. The vial was tilted and 100 μL of a 50 wt % aqueous multi-arm PEG amine solution (P8-10-1) was added with care taken not to mix the two solutions. A timer was started and the two solutions were stirred together with the wooden end of a cotton swab. The initial gel time was defined as the observation of increased viscosity, such that a string formed when the wooden stirring rod was pulled from the gel. The final gel time was defined as the second when stirring pulled the gel from the sides of the vial so that the gel could be removed as the wooden stirring rod was pulled from the vial.

The initial and final gel times are given in Table 5. The final gel times ranged from 4 to 7 sec.

TABLE 5

Gel Times for Forming Hydrogels from Aminated Dextran Aldehydes and P8-10-1 PEG Amine

| Example | Aminated Dextran Aldehyde | Initial Gel Time (sec) | Final Gel Time (sec) |
|---|---|---|---|
| 13 | $DA^1$ = 20% $Am^2$ = 19% | 2 | 7 |
| 14 | DA = 9.5% Am = 38% | 2 | 5 |
| 15 | DA = 49% Am = 12% | 2 | 4 |
| 16 | DA = 51% Am = 18% | 3 | 5 |

[1]DA means dialdehyde content.
[2]Am means amine substitution level.

What is claimed is:

1. A kit comprising: a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; and b) at least one water-dispersible, multi-arm amine wherein at least three of the arms are terminated by a primary amine group, wherein the multi-arm amine has a number-average molecular weight of about 450 to about 200,000 Daltons.

2. The kit according to claim 1, wherein the oxidized polysaccharide is a first aqueous solution or dispersion and the multi-arm amine is a second aqueous solution or dispersion.

3. The kit according to claim 1, wherein the oxidized polysaccharide and the multi-arm amine are finely divided powders.

4. The kit according to claim 1, wherein the oxidized polysaccharide containing aldehyde groups and amine groups is derived from a polysaccharide selected from the group consisting of dextran, carboxymethyldextran, starch, agar, cellulose, hydroxyethylcellulose, carboxymethylcellulose, pullulan, inulun, levan, agarose, and hyaluronic acid.

5. The kit according to claim 1, wherein the oxidized polysaccharide containing aldehyde groups and amine groups is oxidized diethylaminoethyl dextran or oxidized aminated dextran.

6. The kit according to claim 1, wherein the multi-arm amine is selected from the group consisting of water dispersible multi-arm polyether amines, amino-terminated dendritic polyamidoamines, and branched end amines.

7. The kit according to claim 6, wherein the water dispersible multi-arm polyether amines are selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

8. The kit according to claim 1, wherein the oxidized polysaccharide containing aldehyde groups and amine groups is oxidized diethylaminoethyl dextran or oxidized aminated dextran and the multi-arm amine is a multi-arm polyethylene glycol amine.

9. A dried hydrogel product formed by a process comprising the steps of: a) reacting in a solvent (i) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehydes group of about 90 to about 1500 Daltons and an amine substitution level of about 5% to about 50%; with (ii) at least one water-dispersible, multi-arm amine wherein at least three of the arms are terminated by a primary amine group, wherein the multi-arm amine has a number-average molecular weight of about 450 to about 200,000 Daltons to form a hydrogel; and b) treating the hydrogel to remove at least a portion of said solvent to form the dried hydrogel.

10. The dried hydrogel according to claim 9, wherein said dried hydrogel is a film.

11. The dried hydrogel according to claim 9, wherein the process further comprises the step of comminuting the dried hydrogel to form finely divided particles.

12. A composition for coating an anatomical site, the composition comprising the reaction product of:
a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; and b) at least one water-dispersible, multi-arm amine wherein at least three of the arms are terminated by a primary amine group, wherein the multi-arm amine has a number-average molecular weight of about 450 to about 200,000 Daltons.

13. A composition for bonding at least two anatomical sites together, the composition comprising the reaction product of:

a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; and b) at least one water-dispersible, multi-arm amine wherein at least three of the arms are terminated by a primary amine group, wherein the multi-arm amine has a number-average molecular weight of about 450 to about 200,000 Daltons.

14. A product for coating an anatomical site, the product comprising the dried hydrogel of claim 9.

15. A method for applying a coating to an anatomical site on tissue of a living organism, the method comprising applying to the site:

a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; followed by b) at least one water-dispersible, multi-arm amine wherein at least three of the arms are terminated by a primary amine group, wherein the multi-arm amine has a number-average molecular weight of about 450 to about 200,000 Daltons; or applying (b) followed by (a); and mixing (a) and (b) on the site; or premixing (a) and (b) and applying the resulting mixture to the site; or applying (a) and (b) simultaneously to the site.

16. The method according to claim 15 wherein the oxidized polysaccharide is in the form of a first aqueous solution or dispersion and the multi-arm amine is in the form of a second aqueous solution or dispersion.

17. The method according to claim 15 wherein the oxidized polysaccharide and the multi-arm amine are in the form of finely divided powders.

18. The method according to claim 15 wherein the oxidized polysaccharide is diethylaminoethyl dextran or aminated dextran and the multi-arm amine is a multi-arm polyethylene glycol amine.

19. A method for bonding at least two anatomical sites together comprising applying to at least one of the at least two anatomical sites:

a) at least one oxidized polysaccharide containing aldehyde groups and amine groups, wherein said amine groups are not primary amine groups, having a weight-average molecular weight of about 1,000 to about 1,000,000 Daltons, said oxidized polysaccharide having an equivalent weight per aldehyde group of about 90 to about 1500 Daltons and an amine substitution level of about 5% to about 50%; followed by b) at least one water-dispersible, multi-arm amine wherein at least three of the arms are terminated by a primary amine group, wherein the multi-arm amine has a number-average molecular weight of about 450 to about 200,000 Daltons; or applying (b) followed by (a); and mixing (a) and (b) on the at least one site; or premixing (a) and (b) and applying the resulting mixture to the at least one site; or applying (a) and (b) simultaneously to the at least one site; and contacting the at least two anatomical sites together.

20. The method according to claim 19 wherein the oxidized polysaccharide is in the form of a first aqueous solution or dispersion and the multi-arm amine is in the form of a second aqueous solution or dispersion.

21. The method according to claim 19 wherein the oxidized polysaccharide and the multi-arm amine are in the form of finely divided powders.

22. The method according to claim 19 wherein the oxidized polysaccharide is diethylaminoethyl dextran or aminated dextran and the multi-arm amine is a multi-arm polyethylene glycol amine.

23. A method for applying a coating to an anatomical site on tissue of a living organism comprising applying to the site the dried hydrogel of claim 9.

24. The method according to claim 23 wherein said dried hydrogel is in the form of a film.

25. The method according to claim 23 wherein said dried hydrogel is in the form of finely divided particles.

* * * * *